(12) United States Patent
Gilbert

(10) Patent No.: US 10,989,543 B2
(45) Date of Patent: Apr. 27, 2021

(54) CONTROLLER

(71) Applicant: Intercept IP Ltd, Huddersfield (GB)

(72) Inventor: Wayne Gilbert, Bristol (GB)

(73) Assignee: Intercept IP Ltd, Huddersfield (GB)

( * ) Notice: Subject to any disclaimer, the term of this patent is extended or adjusted under 35 U.S.C. 154(b) by 214 days.

(21) Appl. No.: 15/773,936

(22) PCT Filed: Nov. 7, 2016

(86) PCT No.: PCT/GB2016/053483
§ 371 (c)(1),
(2) Date: May 4, 2018

(87) PCT Pub. No.: WO2017/077349
PCT Pub. Date: May 11, 2017

(65) Prior Publication Data
US 2018/0321052 A1 Nov. 8, 2018

(30) Foreign Application Priority Data

Nov. 5, 2015 (GB) .................................. 1519510

(51) Int. Cl.
| | |
|---|---|
| G01C 21/26 | (2006.01) |
| H04W 4/70 | (2018.01) |
| G08G 1/01 | (2006.01) |
| G08G 1/0967 | (2006.01) |
| H04L 29/08 | (2006.01) |

(Continued)

(52) U.S. Cl.
CPC ............. *G01C 21/26* (2013.01); *G01C 21/36* (2013.01); *G08G 1/0112* (2013.01);
(Continued)

(58) Field of Classification Search
CPC ...................................................... G01C 21/36
See application file for complete search history.

(56) References Cited

U.S. PATENT DOCUMENTS

| 6,067,565 A | * | 5/2000 | Horvitz | ................... | H04L 29/06 |
| | | | | | 709/218 |
| 8,681,969 B1 | * | 3/2014 | Rodde | ..................... | H04L 65/80 |
| | | | | | 348/14.02 |

(Continued)

FOREIGN PATENT DOCUMENTS

| EP | 1806880 A1 | 7/2007 |
|---|---|---|
| EP | 2705707 A1 | 3/2014 |
| WO | 2017077349 A1 | 5/2017 |

OTHER PUBLICATIONS

International Search Report and Written Opinion by the ISA/EP, dated Jan. 26, 2017, re PCT Application No. PCT/GB2016/053483.

(Continued)

*Primary Examiner* — Alex C Dunn
(74) *Attorney, Agent, or Firm* — Timmer Law Group, PLLC

(57) ABSTRACT

A controller for managing data demand to and from an asset is described. In particular, the controller is configured to obtain streams of local data from one or more local data sources, said local data providing local information of a current condition of the asset. Once received, the controller determines one or more potential future conditions of the asset based on the current condition of the asset and on changes in the local data. A bandwidth requirement is then determined to obtain streams of remote data from one or more remote data sources potentially relevant to the one or more potential future conditions. This bandwidth requirement is then compared to an available bandwidth; and a priority order determined for obtaining the remote data if the available bandwidth is below the bandwidth requirement.

20 Claims, 6 Drawing Sheets

(51) Int. Cl.
  *H04L 29/06* (2006.01)
  *G01C 21/36* (2006.01)
  *G16H 10/60* (2018.01)
  *G16H 40/67* (2018.01)
(52) U.S. Cl.
  CPC ......... *G08G 1/0129* (2013.01); *G08G 1/0141* (2013.01); *G08G 1/096716* (2013.01); *G08G 1/096741* (2013.01); *G08G 1/096775* (2013.01); *H04L 65/80* (2013.01); *H04L 67/12* (2013.01); *H04L 67/125* (2013.01); *H04L 67/322* (2013.01); *H04W 4/70* (2018.02); *G16H 10/60* (2018.01); *G16H 40/67* (2018.01)

(56) References Cited

U.S. PATENT DOCUMENTS

| | | | | |
|---|---|---|---|---|
| 9,202,375 | B2* | 12/2015 | Sampedro Diaz ... | G08G 1/0969 |
| 10,635,110 | B2* | 4/2020 | Shashua ............... | G05D 1/0287 |
| 2007/0233369 | A1* | 10/2007 | Ng ......................... | G01C 21/26 |
| | | | | 701/532 |
| 2010/0017121 | A1* | 1/2010 | Diaz .................... | G08G 1/0969 |
| | | | | 701/533 |
| 2011/0302236 | A1 | 12/2011 | Shrum et al. | |
| 2012/0056746 | A1* | 3/2012 | Kaigler ................. | A61B 5/0022 |
| | | | | 340/573.1 |
| 2014/0156806 | A1 | 6/2014 | Karpistsenko et al. | |
| 2015/0112883 | A1* | 4/2015 | Orduna ................ | G06Q 50/265 |
| | | | | 705/325 |
| 2015/0222560 | A1 | 8/2015 | Kakadia et al. | |
| 2016/0286506 | A1* | 9/2016 | Chae .................... | H04L 5/0051 |
| 2019/0384294 | A1* | 12/2019 | Shashua ........... | G08G 1/096805 |

OTHER PUBLICATIONS

International Preliminary Report on Patentability by the IPEA/EP, dated Feb. 9, 2018, re PCT Application No. PCT/GB2016/053483.

* cited by examiner

CONTROLLER

FIELD

The present disclosure relates to a controller. In particular, it relates to a controller and system and method for managing data demand to and from an asset.

BACKGROUND

As the number of internet enabled devices, sometimes called smart devices, continues to rise, leading towards an Internet of Things (IoT) world where any and all devices are continually exchanging data, the data analysis and bandwidth requirements also rise. The local data provided by local data sources such as sensors local to devices or assets and the remote data supplied to devices or assets from remote data sources all require an increasing amount of data bandwidth. This trend is set to continue as more devices become 'smart' and as the number and type of local and remote data sources rises.

Whilst the data or information provided by such devices or sensors is useful, it has proved difficult to undertake cross-analysis of seemingly unrelated conditions or data from different devices. Coupled to this is a data and bandwidth management issue where the local data provided by an asset, such as by sensors, together with remote data from remote data sources, such as a server, all have a bandwidth requirement that must be transmitted and received by a controller. When the available bandwidth is greater than the required bandwidth to upload the local data back to a server and to download remote data from the server, the controller is able to analyse the data and make decisions accordingly. However, when the available bandwidth is less than required the controller still attempts to process all the tasks irrespective of the available bandwidth. This can lead to degradation of performance, or for the calculation to halt, pending the arrival of required updated data from the remote data sources.

Currently, the controllers used by such smart devices fail to adequately prioritise data critical to the condition of the asset or device or, in scenarios where the controller does prioritise this is based on a pre-set priority that is not contextual to the current or potential future condition of the device or asset. It can be appreciated that the refresh rate of information supplied by remote data sources can vary depending upon the timing and/or the location of the device or asset. Accordingly, basing decisions on a pre-set non-dynamic work flow or task sequence may lead to errors in decision making by the controller, or potentially an incorrect decision being made by the controller.

A further issue is in the handling of such large volumes of data. US 20140156806 relates to systems and methods for collecting, integrating, processing, distributing, and analyzing spatial and/or spatio-temporal information associated with a variety of data sources and/or locations. Visualizations may be created using such data, and/or analytical queries performed based on the data.

Where bandwidth management has been considered, the known systems rely on prefetching techniques, such as in U.S. Pat. No. 6,067,565 or utilising varying encoding to maximise bandwidth use, such as in US 20110302236. These techniques fail to prioritise based on local conditions of an asset instead determining a priority based on the requirements of the user, not the system.

Similarly, applications that rely on prioritising based on a device backlog or workflow, such as US 20150222560 are intended to manage dataflow and capacity on large networks of devices rather than managing a task priority within a single device.

EP2705707 describes an example of optimizing paths for mobile communications—based on a comparison between a user's current location and intended location, a route is determined for the user that ensures a minimum data bandwidth along the route. However, this method is still reliant on inputs from the user, so cannot necessarily adapt quickly or automatically to real-time events or changes in the condition of the user.

As an example, sensors within motor vehicles are becoming more common. Such sensors typically monitor the speed, direction and even road conditions or weather of the motor vehicle at any point in time. Commonly such sensors are used to determine accident events and for insurance purposes.

Whilst such sensors and detectors are useful, they generally provide data in a manner akin to a black box in an aircraft. The sensors are continually recording data, and whilst algorithms may be utilised to increase or decrease the data sampling rate from the sensors based on predetermined criteria, such algorithms are typically based on complimentary information from one of the other sensors. Additionally, the information is locally based. In other words, information detailing a road traffic accident is only analysed after the accident has occurred.

Typically, continuing the road traffic accident example, such events are not so clearly linearly based on only one or two parameters. Accidents or events may be correlated to other factors, including the location of the motor vehicle relative to other motor vehicles; the speed of such other motor vehicles; the driving style of the driver of the motor vehicle or such other motor vehicles; the weight of the motor vehicle; the condition of the motor vehicle, etc. Whilst such information could be collated from individual sensors on the motor vehicles involved, laborious correlation calculations would be required to determine the key reasons for the accident.

Even more preferable would be the ability to pre-empt and prevent such accidents from occurring. For example by analysing the likelihood of two vehicles colliding and, if the risk becomes too high, taking measures to prevent a collision.

One potential area of interest is autonomous vehicles, or at least smart vehicles. In such assets or devices, the vehicle has a central controller that acts to receive local data information from local data sources, such as sensors. This local data may be uploaded to a remote server typically using a wireless protocol. Additionally, the controller may receive information from the remote server or from another remote server with remote data. However, at present, these two requirements compete for data bandwidth and continually attempt to refresh data sent to or from the controller and the server (or operate on a fixed time based refresh rate). There is no contextualisation based on the status or current condition or potential future condition of the vehicle. This leads to a waste of bandwidth, data congestion, and potential issues in areas of low bandwidth.

A further area of potential interest is medical technology. Smart medical devices, such as smart watches, provide a continual stream of medical data about a user to and from an external server, this medical data is sometimes referred to as health and usage monitoring system (HUMS) data. As with the vehicle example, such smart medical devices typically comprise a plurality of sensors that determine and update the remote server on the condition of the user. However, like the vehicle example, such sensors typically provide the information at fixed intervals and lack contextualisation based on the condition (current or future) of the user.

Robotics is another area of potential interest. Robotics utilise cybernetic data such as the control, sensory feedback and information processing data, which can be a combination of local data and remote data. It can be appreciated that bandwidth management issues may also require management to ensure that the robot prioritises obtaining remote data in a similar manner to described above.

It is an object of the present invention to ameliorate or alleviate the aforementioned drawbacks described above.

SUMMARY

According to a first aspect of the present invention, there is disclosed a controller for managing data demand to and from an asset, wherein the controller is configured to: obtain streams of local data from one or more local data sources, said local data providing local information of a current condition of the asset; determine one or more potential future conditions of the asset based on the current condition of the asset and on changes in the local data; determine a bandwidth requirement to obtain streams of remote data from one or more remote data sources potentially relevant to the one or more potential future conditions; compare the bandwidth requirement to an available bandwidth; and determine a priority order for obtaining the remote data if the available bandwidth is below the bandwidth requirement.

The controller described herein may be considered as providing a framework to allow assets to combine local data sources with remote potentially relevant data sources to improve decision making. The assets can include connected devices, such as those found in Internet of Things (IoT) devices, as well as specific examples to be described below.

The controller may be considered to act to manage the bandwidth of upstream and/or downstream data traffic depending upon the bandwidth availability and the priority of the data flow.

In embodiments, the controller may be further configured to priority order by calculating the relevance of the remote data to the one or more potential future conditions based on changes in the local data. Some of the remote data may lack relevance to the one or more potential future conditions. In particular, the controller may be interested in how the remote data varies with respect to the potential future conditions when compared to the current condition of the asset. If there is no time or position relationship between the current condition, the potential future conditions and the remote data, then the relevance is likely to be low. Conversely, remote data that is coupled with and varies depending on the time and/or position of the asset is likely to have a higher relevance.

As noted above, changes in the current condition of the asset may be assessed locally by changes in the local data. Calculations involving these local data sources may be used to dynamically alter the priority order to prioritise obtaining the most relevant remote data in order of relevance within the available bandwidth.

In embodiments, the controller may determine the order of relevance based on an event sequence describing a task priority for handling of the remote data. The event sequence typically provides an initial or best-case ranking of the remote data to allow the controller to request the remote data according to the task priority. The event sequence may be dynamically altered based on the available bandwidth.

The event sequence may revert or default to a root sequence defining a default task priority for handling of remote data if the available bandwidth is at or above the determined bandwidth requirement. The event sequence may also default to the root sequence if the available bandwidth is insufficient to obtain any remote data sources.

The root sequence may revert or default to the root sequence if the asset determines that there is insufficient data to determine the relevance of the remote data to the one or more potential future conditions.

The event sequence may further describe the task priority for handling of the local data. The event sequence may be considered to be the mechanism by which the controller ensures that critical services are maintained or decisions reached.

The event sequence may comprise one or more data planes of remote data and local data, said data planes defining the one or more potential future conditions.

In embodiments, a data plane may be populated by: the remote data from the one or more remote data sources; and the local information from the one or more local data sources. Each data plane may have a downstream bandwidth requirement for obtaining the remote data from the one or more remote data sources. The bandwidth requirement may be considered to be the sum of the downstream bandwidth requirements for every data plane. Each data plane may also have an upstream bandwidth requirement for reporting the local data or changes in the local data to a remote server. The bandwidth requirement may be considered to be the sum of the upstream and downstream bandwidth requirements for every data plane Each stream of local and remote data may be represented by a single stream, or one or more streams may be combined into a multi-dimensional stream. The data planes may combine the local and remote data based on a location of the asset. The data planes may be arranged in a tensor. Depending upon the relationship between the streams of data within the data plane, or between the data streams themselves, the tensor may be a scalar, vector or matrix of varying dimensionality. Such an arrangement of data streams allows the controller to tailor the root sequence by modifying, deleting, restoring or otherwise manipulating the data planes to alter the priority and relevance of the data planes during calculations. The data planes may be arranged according to the event sequence. It can be appreciated that different event sequences may be determined for each of the one or more potential future conditions.

In further embodiments, the controller may be further configured to assign a critical time value to each potential future condition that defines the time by which the potential future condition requires refreshed remote data. This critical time value may be considered to be the maximum time that the remote data from a remote data source is considered valid. The critical time value may be different for the same data source for different potential future conditions and may vary depending upon the previous value of the remote data provided.

The controller may calculate a remote bandwidth required to obtain the remote data within the critical time value for one or more of the potential future conditions or for each potential future condition. This remote bandwidth can be considered to be the bandwidth requirement for the remote data during the critical time value. In other words, this remote data will require a refresh within the critical time value, which will require the remote bandwidth value. Accordingly, the bandwidth requirement may be considered to comprise the sum of the remote bandwidth required for all potential future conditions. In embodiments, the controller may be further configured to determine which potential future conditions are most probable. The bandwidth requirement may then comprise the sum of the remote bandwidth required for the most probable potential future conditions.

The controller may be further configured to alter the behaviour of the asset to mitigate any risk associated with the most probable potential future conditions if the available bandwidth is below the bandwidth requirement for longer than the critical time. Similarly, the controller may alter the behaviour of the asset to mitigate any risk associated with the one or more potential future conditions if the available bandwidth is below the bandwidth requirement for longer than each potential future condition's critical time. In other words, if the bandwidth is insufficient to refresh the remote data during the critical time, the controller may be configured to mitigate the risk associated with the most probable or any future conditions reliant on unavailable refreshed remote data.

The bandwidth requirement may comprise the bandwidth required to transmit the local data from the asset to a server. Additionally or alternatively, the bandwidth requirement may comprise the bandwidth required to transmit changes in the local data to the or a server.

The controller may be further configured to determine the one or more potential future conditions of the asset based on one or more potential future locations of the asset. This provides a contextual analysis for potential future conditions of the asset based on current data describing the location of the asset, the velocity (speed and direction) of the asset and other factors, such as expected destination or route, weather conditions, etc.

In embodiments, the controller may be further configured to predict the available bandwidth based on the potential future locations of the asset. The controller may receive remote data describing the available data bandwidth in the current and all expected locations of the asset. This can allow the controller to alter the priority or relevance of the remote data to account for this expected reduction in bandwidth. For example, where applicable, any remote data having a critical time due to require refresh within the reduced bandwidth region may be brought forward or prioritised out of usual turn to allow the data to be refreshed in a current region or location of sufficient bandwidth.

In embodiments, the asset may be a vehicle, typically a motor vehicle. Other vehicles may also be suitable, such as boats, helicopters, aeroplanes, etc.

The asset may be a health device. Such health devices can include smart watches, ambulatory medical devices such as insulin pumps or other such devices.

The asset may be a robotic device. Such robotic devices may include robots.

The local data sources may be sensors monitoring the condition of the asset.

Such sensors may typically include for a vehicle asset: condition sensors, such as on board diagnostic systems obtaining data relating to brake pad thickness, suspension stiffness, engine data, drivetrain data, tyre pressures and wear etc.; environmental sensors, such as LIDAR for determining distances between the vehicle and other objects, rain sensors, temperature sensors etc.; contextual sensors, such as occupancy sensors, GPS data etc.; and/or media sensors such as audio/visual media, heads-up display data etc.

Such sensors may typically include for a health device: health diagnostic sensors, such as heart rate and rhythm sensors, blood glucose level, etc.; activity sensors, such as movement sensors including accelerometers, gyrometers; body position sensors including gyrometers; location sensors including GPS and wireless communication positioning sensors; and user status sensors, such as body temperature using a thermometer.

Such sensors may typically include for a robotic device: control sensors for detecting and controlling movement of the robot, sensory feedback sensors for detecting and monitoring the robots position and context to other devices and assets and information processing data sensors that detect and regulate the flow and processing of data.

The remote data sources may be stored on and/or transmitted by a server or a cloud based server.

The potentially relevant remote data may typically include for a vehicle asset: live and/or historical road traffic congestion information; traffic flow; historical road based accident statistics; current predictions of short term local weather conditions vehicle performance data; historic driver reaction time data; and bandwidth availability by geographic location. It can be appreciated that some or all of the remote data is contextual based on the local information from the local data.

The potentially relevant remote data may typically include for a medical device: patients previous medical history, including typical heart rhythm and medication history; normal heart rhythm under various stress factors e.g. exercise, heat etc.; local weather conditions; local mapping to show gradient of an intended exercise or walking route; bandwidth availability by geographic location and air quality levels. It can be appreciated that some or all of the remote data is contextual based on the local information from the local data.

The potentially relevant remote data may typically include for a robotics device: geolocations of other robots; predictions of future demand; bandwidth availability by geographic location, or other remote based data. It can be appreciated that some or all of the remote data is contextual based on the local information from the local data.

According to a second aspect of the present invention, there is provided a system for managing data demand to and from an asset, said system comprising: a controller according to any embodiment of the first aspect; and an output channel associated with the controller and configured to transceive the streams of remote data to and from the controller.

In embodiments, the output channel may comprise a plurality of data communication devices, such as wireless fidelity and/or wireless mobile telecommunications technology, which includes radio based telecommunications.

According to a third aspect of the present invention there is provided a method of managing data demand for an asset, said method comprising the steps of: receiving streams of local data from one or more local data sources, said local data monitoring a current condition of the asset; identifying changes in the current condition of the asset from changes in the local data sources; determining one or more potential future conditions of the asset based on the changes; determining a bandwidth requirement for obtaining streams of remote data from one or more remote data sources relevant to the one or more potential future conditions; and comparing the bandwidth requirement to an available bandwidth; and prioritising the order in which the streams of remote data are retrieved.

In embodiments, the method may prioritise the order based on the bandwidth requirement of each stream of data. In other or related embodiments the order may be based on a time criticality for refreshing the remote data.

In an alternative aspect of the present invention, there is provided a controller for managing data demand to and from an asset, wherein the controller is configured to: obtain local data from one or more local data sources, said local data providing local information of a current condition of the asset; determine one or more potential future conditions of the asset based on the current condition of the asset and on changes in the local data; determine a bandwidth requirement for obtaining remote data from one or more remote data sources potentially relevant to the one or more potential future conditions; determine an event sequence order for obtaining the remote data, based on the local data; and obtain the remote data according to the event sequence order.

In this aspect, the controller may be further configured to: compare the bandwidth requirement to an available bandwidth; and modify the event sequence order if the available bandwidth is below the bandwidth requirement. The controller may be further configured to determine the relevance of the remote data to the one or more potential future conditions. The controller may also be further configured to dynamically modify the event sequence order to prioritise obtaining the remote data in order of relevance within the available bandwidth. Furthermore, the event sequence order may be determined based on a pre-set root sequence order.

For all aspects, it may also be envisaged that multiple systems or controllers can interact to influence the state of events of each system—so each system or controller acts as a transmitter providing remote data to other systems or controllers. Continuing with the motor vehicle example, systems or controllers may interact based on their relative road position, relative weights (stopping distances), relative speeds, relative vehicle conditions etc. to alter the state of events. For example, a vehicle, which in isolation is at a low risk of accident can be adversely affected by another vehicle with a higher risk, for example with failed or degraded brakes on a collision course at a junction.

By using the described to prioritise the multiple data streams of each system, only the relevant data streams need to be considered if the bandwidth is insufficient to allow all streams to be updated or considered—data streams which are unrelated to the event are constant or uncorrelated and may provide a constant, unchanging contribution to the state of the event, namely the current condition of the asset and the potential future conditions of the asset.

According to another example of the present disclosure, there is described a method of handling data, said method comprising the steps of: collating a plurality of streams of data from at least one system, the streams of data collectively representing a state of an event, wherein at least one of the streams of data is a time dependent data stream; relaying the streams of data to a server; determining any dependence between one or more of the streams of data and the one or more time dependent data streams to identify coupling variables; forming a multi-dimensional tensor having the coupling variables as components of the tensor; calculate one or more invariants of the multi-dimensional tensor; and defining the state of the event based on the values of the calculated invariants.

By defining the state of events based on invariants, new data for subsequent events can be easily aggregated and comparisons with earlier events made. This drastically reduces the computational requirement of monitoring how streams of data vary over time. Such methods may be useful for providing feedback to systems highlighting emerging trends in real time, without the need to undertake analysis of specific data streams. This is especially important in systems and events related thereto where a large number of highly variable, interconnected data streams are provided, such as monitoring of motor vehicles. By determining that the state (for example the risk of an accident) of events (such as driving) varies over time or even in real time, this information can be relayed back to the system (the motor vehicle), allowing corrective action to be taken.

In optional examples, at least one system may comprise a plurality of sensors monitoring the state of the event and the plurality of streams of data are collated from the plurality of sensors. The step of collating the data may further comprise the step of: determining data streams from the plurality of streams of data whose values vary within a time window, wherein the time window is selected based on the event or scenario being determined. Furthermore, the step of collating the data may further comprise the step of: determining the time dependence of each data stream. The time dependent data streams may be the data streams which are strongly time dependent.

In examples, the step of determining any dependence may comprise the step of: discretizing the time dependent data streams. The step of discretizing the time dependent data streams may further comprise the step of aggregating the streams of data over a time period. The time period may be selected based on the time dependence of the time dependent data stream. The step of discretizing the data can comprise the step of: forming an occurrence tensor having a length equal to the number of data streams. The step of discretizing the data further may further comprise the steps of: determining a number of occurrences of a data value in each stream of data over the time period; and assigning the components of the occurrence tensor to be the number of occurrences. Furthermore, the time period may be a plurality of time periods, such that an occurrence tensor is formed for each time period. The coupling variables may be the number of occurrences of each aggregate tensor in the time period. Alternatively, the occurrence tensors may be aggregated into a time-dependent event tensor. In examples, the occurrence tensors may be vectors.

An event tensor may be provided that describes one or more data streams. Accordingly, the step of forming a multidimensional tensor may comprise the step of calculating the product of the event tensor and the time-dependent event tensor.

In another example of the present disclosure, there is described a method of determining a current risk state of a motor vehicle, said method comprising the steps of: collating one or more streams of data from one or more event sensors on the motor vehicle, each stream of data representing an risk factor, wherein at least one of the streams of data is a time dependent data stream; relaying the streams of data to a server; determining any dependence between one or more of the streams of data and the one or more time dependent data streams to identify coupling variables; forming a multi-dimensional tensor having the coupling variables as components of the tensor; calculate one or more invariants of the multi-dimensional tensor; and defining the current state of the motor vehicle based on the values of the invariants.

In optional examples, the event sensors may define one or more of: motion of the motor vehicle; location of the motor vehicle relative to other motor vehicles; road surface conditions; weather conditions; the GPS location of the motor vehicle; the speed of the motor vehicle; the driving style of the driver of the motor vehicle; the weight of the motor vehicle; or the condition of the motor vehicle. In this example, the step of forming the multidimensional tensor may comprise the step of: determining a risks tensor that aggregates the risk factors posed to the motor vehicle; and providing a scores tensor that represents how each risk factor contributes to the overall risk posed to the motor vehicle.

It can be appreciated that the event sensors may be the local data, such as provided by local sensors, described in relation to any other the earlier aspects, or may be a combination of the local data and the remote data.

There may be provided a computer program, which when run on a computer, causes the computer to configure any apparatus, including a circuit, controller, sensor, filter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), flash memory, or a chip as non-limiting examples. The software implementation may be an assembly program.

The computer program may be provided on a computer readable medium, which may be a physical computer readable medium, such as a disc or a memory device, or may be embodied as a transient signal. Such a transient signal may be a network download, including an internet download.

Any reference to a server is intended to encompass single processor devices, in addition to multiple processor devices. A server is broadly intended to mean any device external to the immediate system to which data may be transmitted and/or received.

These and other aspects of the disclosure will be apparent from, and elucidated with reference to, the embodiments described hereinafter.

BRIEF DESCRIPTION OF THE DRAWINGS

Embodiments will be described, by way of example only, with reference to the drawings, in which

FIG. 4b is a graphical representation of available bandwidth against time in relation to the representation of FIG. 4a;

Figure 1:
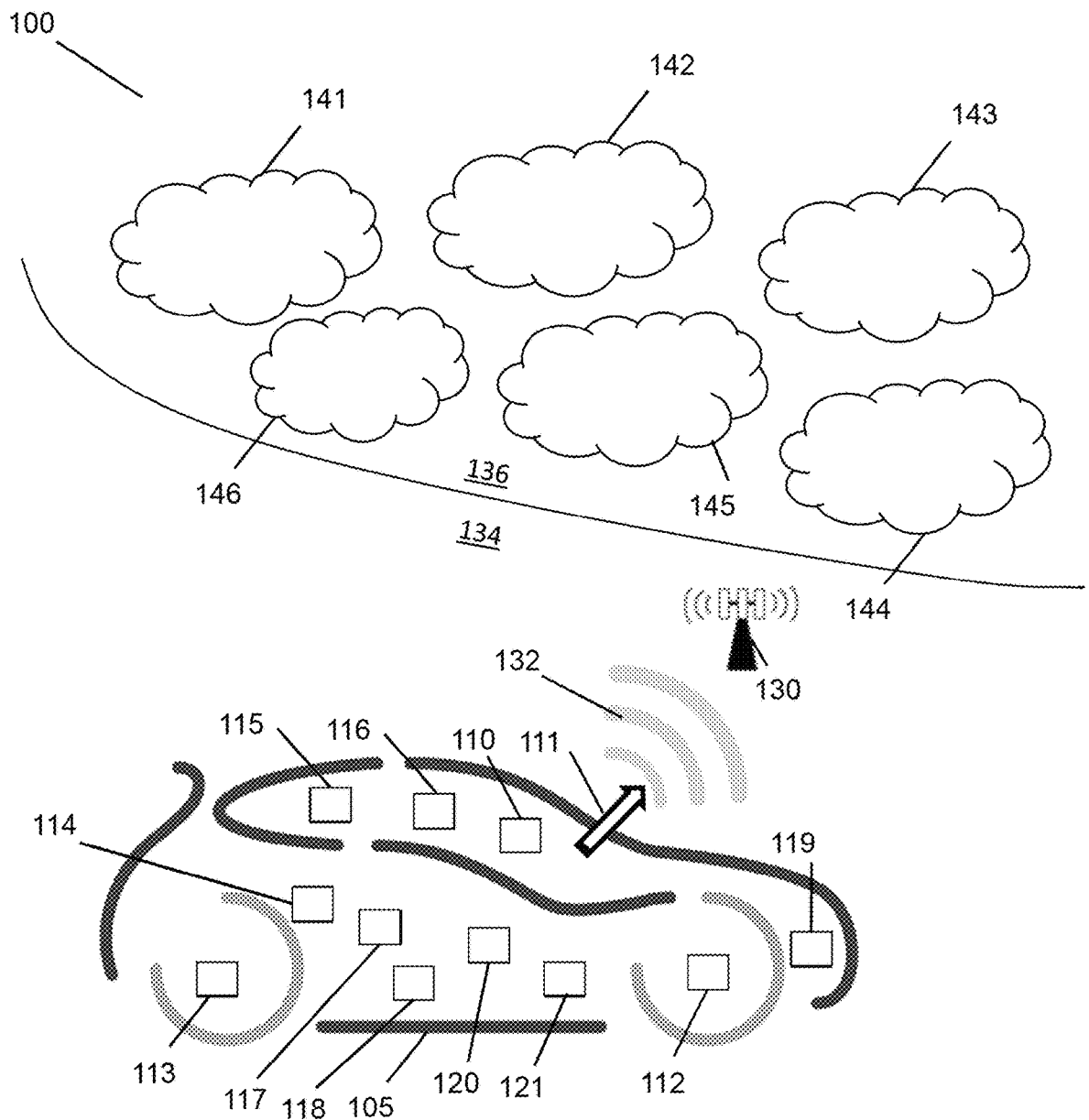
FIG. 1 is a schematic of a system featuring an asset having a controller according to aspects of the present disclosure.

It should be noted that the Figures are diagrammatic and not drawn to scale. Relative dimensions and proportions of parts of these Figures have been shown exaggerated or reduced in size, for the sake of clarity and convenience in the drawings. The same reference signs are generally used to refer to corresponding or similar feature in modified and different embodiments.

DETAILED DESCRIPTION

Throughout the description and claims of this invention, the word "comprise" and variations of the word, such as "comprising" and "comprises", means "including but not limited to" and it does not exclude other components, integers or steps. The same reference numbers in different drawings may identify the same or similar elements.

FIG. 1 is a schematic representation of a system 100 comprising an asset 105 having a controller 110. In the example shown and embodiment described, the asset 105 is a motor vehicle, although it can be appreciated that other assets may be used. Exemplary other assets may include other vehicles or transport devices, such as ships, airplanes, bicycles, etc. Additionally the asset may be a user and the controller may be a health controller. Further examples will be described below. Additionally, although a controller is described, a controller may be considered to be a microprocessor.

In the example of FIG. 1, the asset, a motor vehicle 105, has a controller 110. The controller 110 is provided with an output channel 111. The output channel 111 typically comprises a plurality of data communication devices for communication over a mobile network 134, such as wireless fidelity and/or wireless mobile telecommunication technology, such as GPRS, EDGE, HSDPA, 3G and 4G. It can be appreciated that any suitable, typically wireless, communication standard may be utilised.

The controller 110 is intended for use for managing data demand to and from the vehicle 105 between the vehicle 105 and a remote server or cloud-based service, typically the Internet 136. The vehicle 105 is provided with a plurality of local data sources 112-121. These data sources typically comprise sensors that provide streams of local data to the controller 110 and provide local information of a current condition of the vehicle 105. The sensors typically can include engine sensors 112, tyre wear sensors 113, a global positioning system (GPS) device 114, occupancy sensors 115, environment sensors 116, inertial sensors 117, drivetrain sensors 118, LIDAR sensors 119, displays 120 and media sensors 121. These local sensors provide local data sources that combine to assess the vehicle's current condition. Other local sensors may be provided as necessary—it can be appreciated that more or less sensors may be utilised depending on the configurations of the vehicle and the requirements of the system.

Local sensors 112-121 are configured to continually provide information to the controller 110 and may be set up to provide the local data on a push basis, a refresh time or as called by the controller 110.

The output channel 111 of the controller 110 is configured to act as or in combination with a transceiver 130 to transmit data information from the local sensors 112-121 to a server or the Internet 136. A variable bandwidth 132 is typically utilised.

The transceiver 130 is also configured to receive remote data from one or more potentially relevant remote data sources 141-146 stored in the Internet 136 or at a server. These remote data sources 141-146 may include a prediction of the bandwidth availability along a route 141, road accident data 142, vehicle performance data 143, traffic along the route 144, an indication of typical driver behaviour 145 and a prediction of the weather along the route 146. The remote data provided from these streams may be potentially relevant to one or more potential future conditions of the motor vehicle 105.

For example, it is clear that each one of the local vehicle data sources gives an indication of increased risk to the vehicle. However by combining any or all of the above the risk of the vehicle having an accident can be ascertained more accurately, for example a marginal brake pad warning will require replacement in the near future, but if the car is heavily loaded, in heavy rain with sub-zero temperatures and fairly worn tyres then risk is increased and the car may be unsafe to drive, but if it is a dry, warm day on new tyres with little rear weight then risk is diminished and may involve a warning to avoid high speeds until replacement.

The traditional telematics approach to this is to monitor all of the on-board vehicle data sources and send any out of range data to the server. At the server or cloud the data is combined with the remote analytics data and a calculation made. This calculation is then sent back to the vehicle instructing action to be taken.

The challenge with this approach is that the vehicle may require immediate action and the speed of response is determined by two factors, namely system latency for speed of processing and available bandwidth to transfer the data either way. The increase in both local and remote data volumes compounds this problem.

Figure 2:
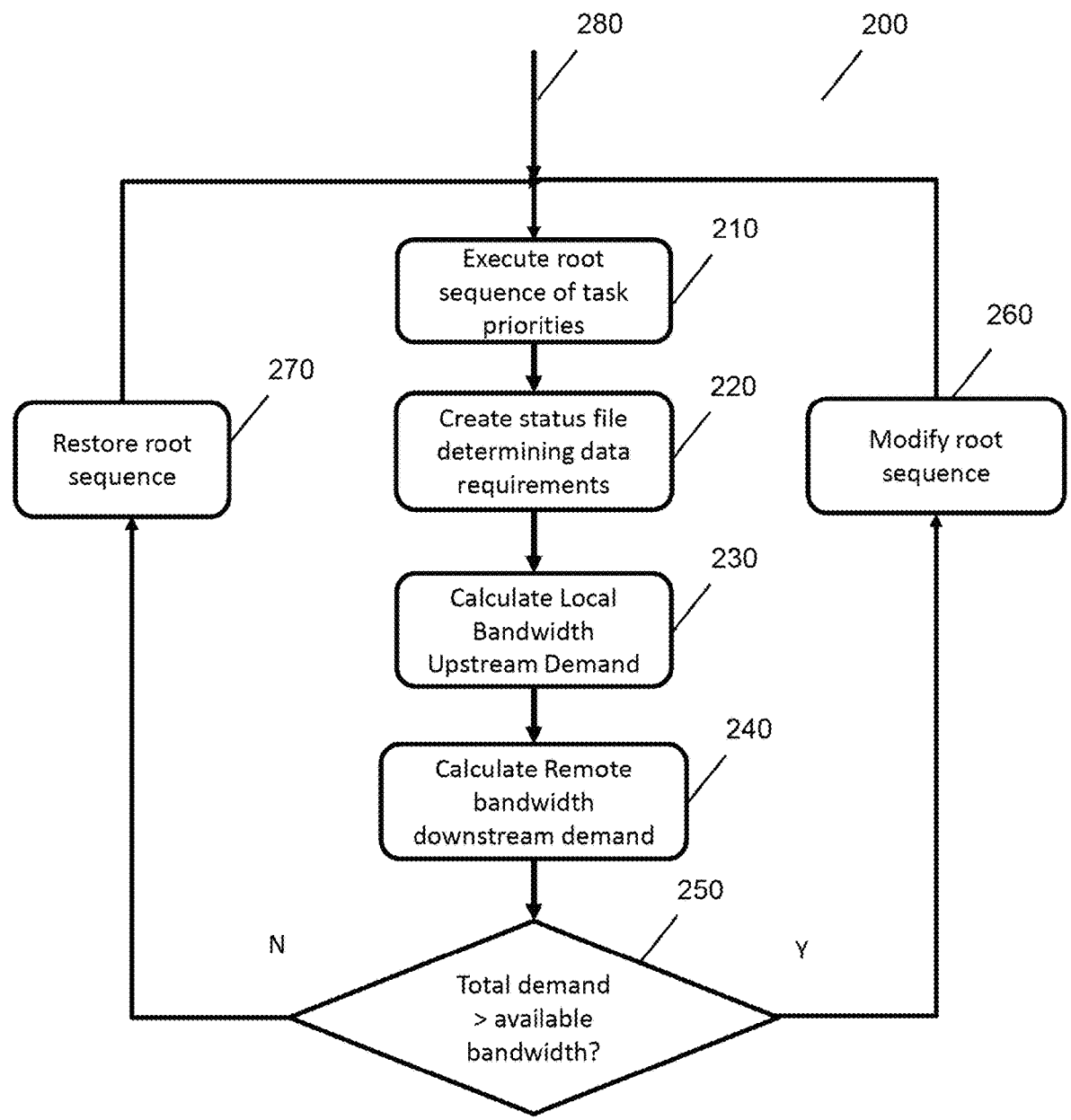
FIG. 2 is a flowchart outlining a process undertaken by the controller of FIG. 1 according to embodiments of the present disclosure.

FIG. 2 is a diagram of a flowchart of an example process 200 undertaken by the controller 110 and described herein. The process 200 generally comprises instructions to the controller to execute a sequence of task priorities according to an order sequence or root sequence 210 which will be described in further detail below. The controller 110 retains the streams of local data from the one or more local data sources 111-121, with the local data providing the local information of the current condition of the vehicle 105.

Next, the controller 110 is configured to determine one or more potential future conditions of the vehicle 105 based on the current condition of the vehicle 105 and on changes in the local data provided by the local data sources 111-121. With this information, the controller may create a status file which determines data requirements 220, such as what additional data is required to determine one or more potential future conditions of the vehicle 105.

A bandwidth requirement can then be calculated to obtain streams of remote data 141-146 from the Internet or from a server. The bandwidth requirement is typically the downstream demand for obtaining the additional data 240, which is typically remote data from the remote data sources 141-146. The upstream demand and local bandwidth required to update the local data from the local data sources 111-121 to the Internet or a server may also be taken into account 230.

Once the bandwidth requirement is known, the controller 110 is configured to compare the bandwidth requirement to an available bandwidth 250. If the total demand for bandwidth is greater than the available bandwidth then the controller 110 is configured to determine a priority order for obtaining the remote data, which may take the form of a modified version of the initial root sequence 260.

If the total demand is lower than the available bandwidth then typically, the initial root sequence is restored 270. The initial root sequence may be pre-set 280 from an external source.

Figure 3:
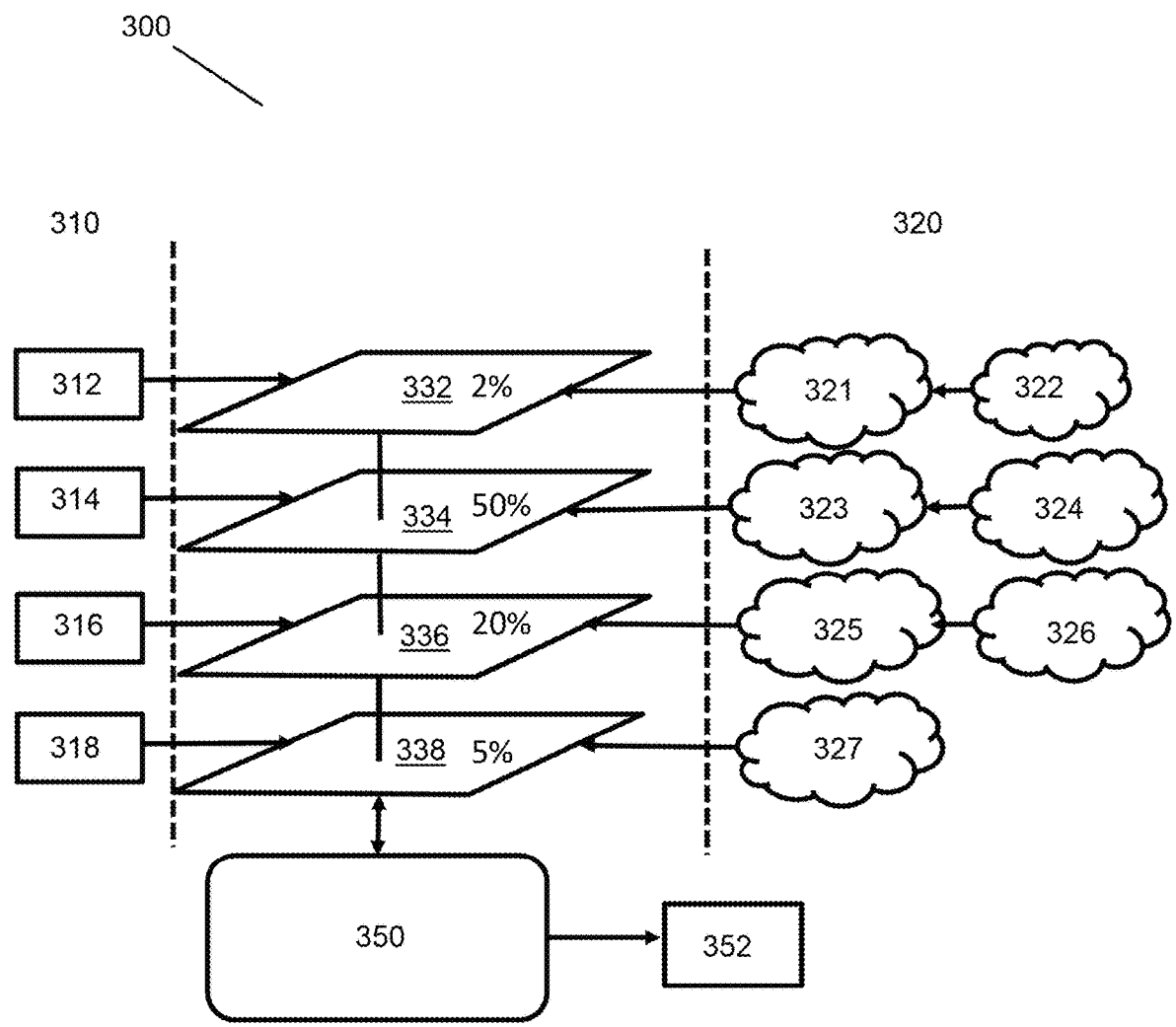
FIG. 3 is a representation of a data plane structure utilised by the controller of FIG. 1 according to an embodiment of the present disclosure.

FIG. 3 shows an embodiment of a representation of the data plane structure 300 utilised by the controller 110. The structure 300 broadly comprises local data in area 310, such as occupancy data 312, media data 314, vehicle dynamic data 316 and engine data 318 together with remote cloud data 320 such as route traffic 321, road accident data 322, root bandwidth prediction 323, root weather prediction 324, vehicle performance data 325, driver behaviour record 326, and vehicle performance data 327. Other relevant remote data may be incorporated as necessary.

This data is configured to be arranged in a plurality of data planes 332, 334, 336 and 338. Each data plane of the data structure combines the local sensor data 310 with remote cloud data 320. For example, plane 332 combines occupancy data 312 with remote data for traffic along the current route 321 and the road accident data for the current route 322. It can be appreciated, that the local sensor data and remote cloud data chosen to populate a particular data plane may be predefined or predetermined or it may be calculated by the processor 110. Additionally, each data plane typically has a bandwidth demand or requirement. In example shown this is represented as a percentage of the currently available bandwidth. So plane 332 requires 2% of the currently available bandwidth, plane 334 requires 50% of the currently available bandwidth, plane 336 requires 20% currently available bandwidth and plane 338 requires 5% of currently available bandwidth. Accordingly, it can be appreciated that the bandwidth requirement is the sum of the bandwidth demand for each plane.

In combination, these data planes define the current condition of the asset as well as likely potential future conditions. These data planes are fed through to the vehicle computer 350 in which the controller 110 may be integrated or comprise. From an analysis of these data planes, the status 352 of the vehicle 105 may be determined, which may include advisory action for either the driver or a controlling processor or computer.

Figure 4A:
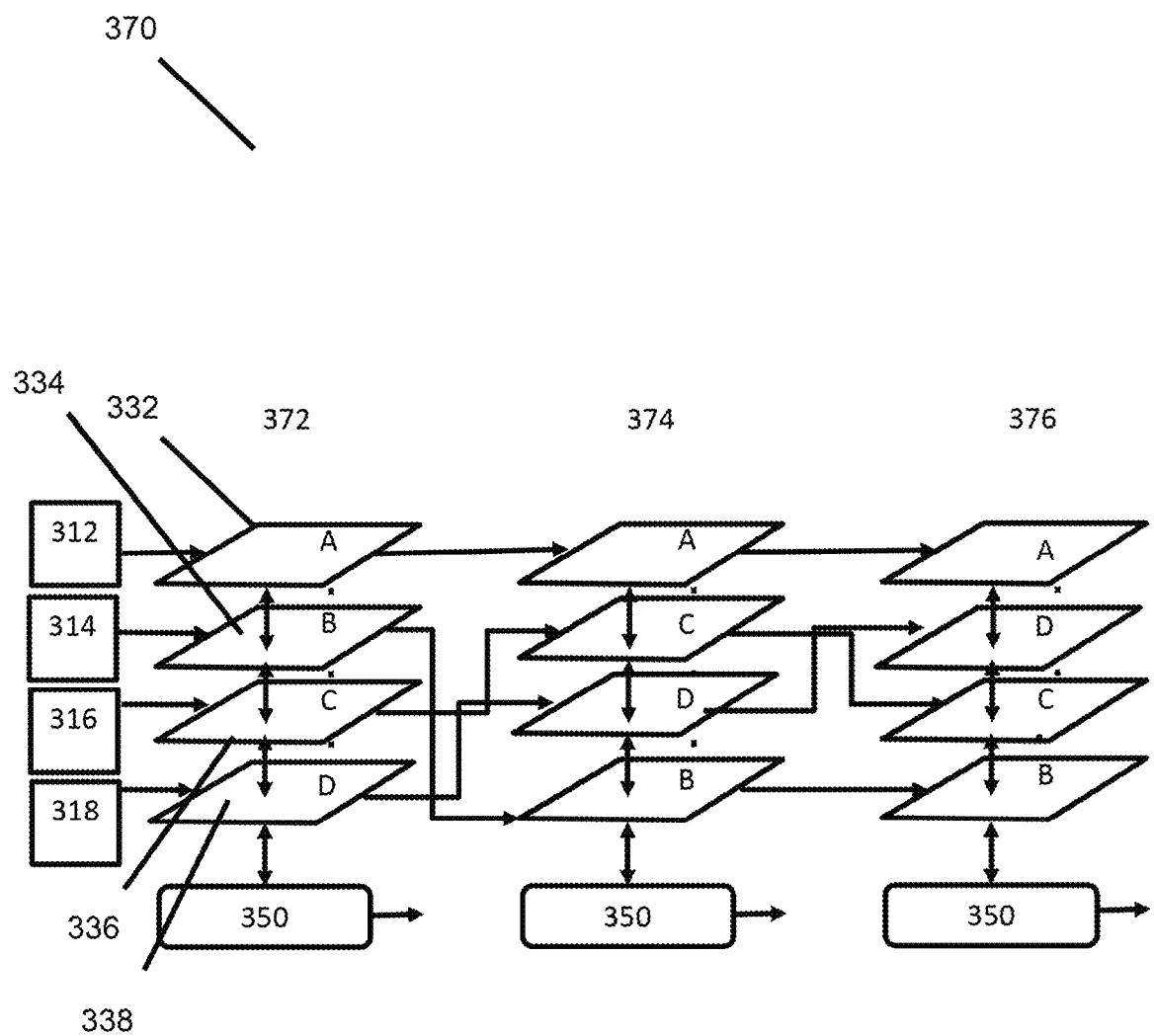
FIG. 4a is a representation of data plane structure ordering utilised by the process of FIG. 1 according to an embodiment of the present disclosure.

In example shown in FIG. 3, the data planes are arranged according to a predetermined priority order, such as the order defined by the root sequence. FIG. 4a illustrates how the priority order may vary. Initially, the data planes 332, 334, 336, 338 labelled A, B, C and D for ease of reference in this figure arranged according to a predefined root sequence 372 as described above.

As described previously, the data planes 332, 334, 336, 338 may be generated based on local data 312, 314, 316, 318 in combination with remote data.

Initially, the available bandwidth is higher than the bandwidth demand for the data planes 332, 334, 336, 338. However, if the available bandwidth decreases as shown by 374a in FIG. 4b, then the controller is configured to rearrange or reorder the data planes 332, 334, 336, 338 in an event sequence to prioritise the most relevant remote data. Accordingly, in the example shown in FIG. 4A at point 374, the remote data associated with plane A will be called first, followed by the remote data associated with plane C, then plane D and finally plane B. Given that plane A relates to remote data relevant to the occupancy of the car 312, plane C relates to remote data relevant to the vehicle dynamics 316, plane D relates to remote data relevant to the engine 318 of the vehicle, whilst plane B relates to media devices 314, during this drop in available bandwidth remote data relevant to media is demoted in priority compared to data relating to the vehicle dynamics and the engine. In example shown, the bandwidth may only be sufficient to refresh remote data relevant planes A and C. The event sequence may default or be preset according to a root sequence that presets the order in which the remote data in the data planes are called. The event sequence may revert to the root sequence if the available bandwidth is greater than the required bandwidth.

Figure 4B:
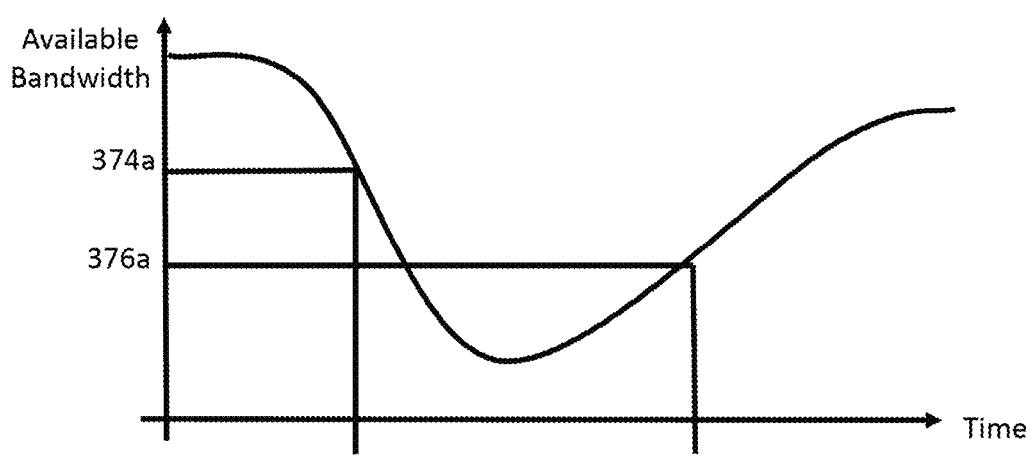

As the available bandwidth continues to vary, such as to the point 376a shown in FIG. 4b, the controller may rearrange the event sequence, which may be referred to as the order sequence, of the data planes 332, 334, 336, 338 as shown at step 376. Here, the available bandwidth is high enough to allow remote data relevant to the engine to be refreshed, shown in plane D, and so plane D is promoted in preference to plane C, which has recently been refreshed. Accordingly, remote data relevant to plane A will be called first, followed by remote data relevant plane D, followed by remote data relevant plane C and, if bandwidth allows, remote data relevant to plane B will be refreshed.

Figure 5:
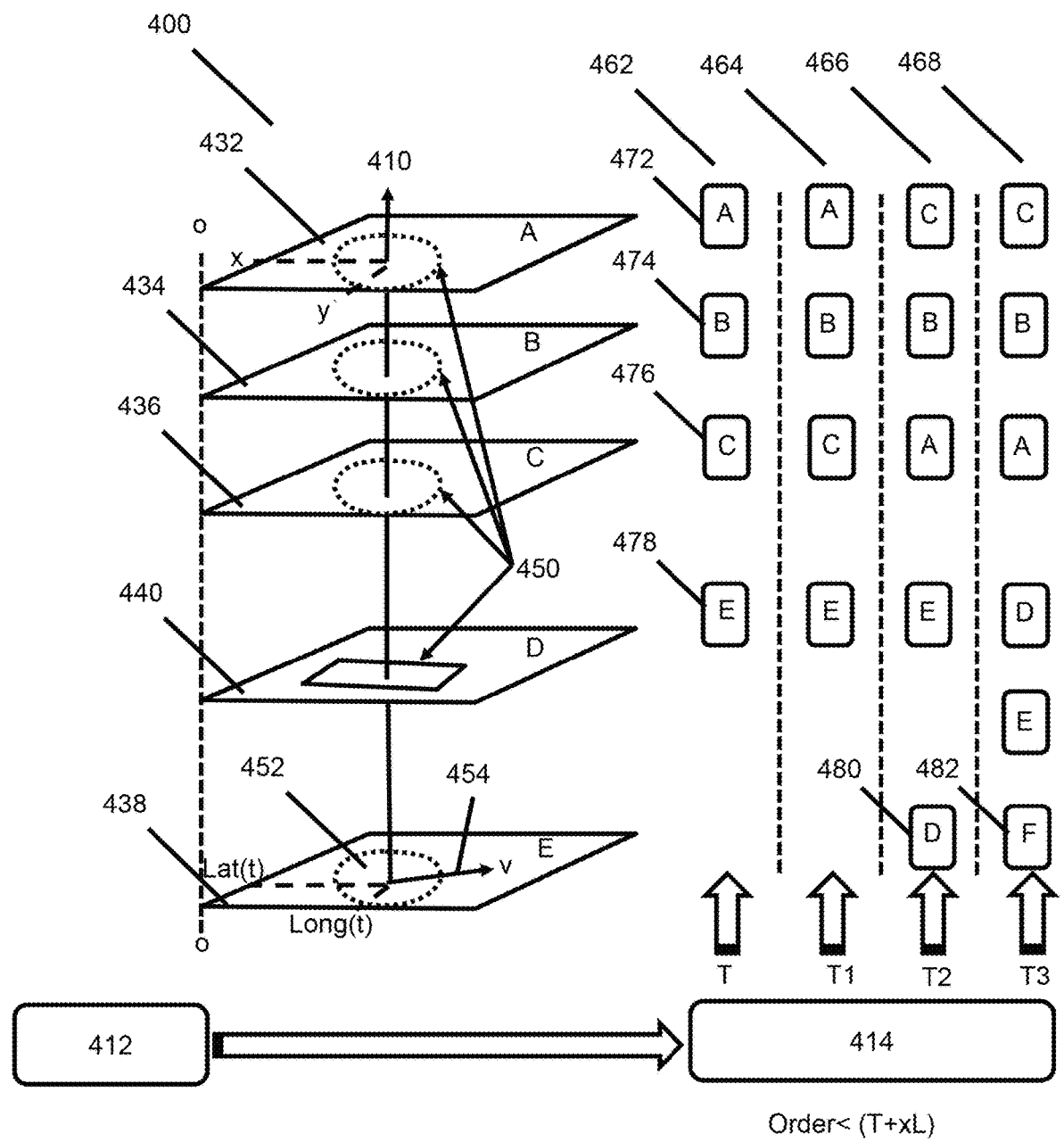
FIG. 5 is a representation of a data plane structure utilised by the controller of FIG. 1 according to an embodiment of the present disclosure.

FIG. 5 illustrates a further embodiment of prioritisation described with reference to FIG. 4. In particular, FIG. 5 shows a data plane structure 400, where the current condition or context of the vehicle is shown by arrow 410, bandwidth processes are shown to the left hand side 412, whilst an indication of the order processes 414 are shown on the right-hand side of the figure.

Similar to FIG. 4, a plurality of data planes 432, 434, 436 and 438 are shown. These data planes relate to occupancy local data, media local data, vehicle dynamics local data and engine local data. Remote data relevant to each data plane is not shown in this figure, however it can be appreciated that the data planes comprise a combination of local and remote data as previously described.

Additionally, a new process and associated new data plane 440 is shown, that may be introduced into the system. This new process and new data plane 440 may be the result of a change in the current context 410 of the vehicle 105, where a modification in local data suggests that an additional data plane is required. For example, environment sensors on the cars may detect that it has begun to rain. Accordingly, the data plane 440 may be a combination of the environmental data from these rain sensors, together with remote data predicting future weather along the current route. It can be appreciated that the data plane 440 may be a combination of alternative local data sources or sensors with alternative remote data sources.

The context 410 of the vehicle 105 or asset defines the current condition of the vehicle or asset, namely the current condition of the asset in the data planes 434, 434, 436, 438. Where the current condition of the asset is likely to change, such as due to a change to or consequence of the likely direction and speed, v 454 of the asset, each plane has a zone of time criticality 450 that predicts the likely future condition of that plane of data based on the current context 410 and the likely changes 454 if the data within the planes is not refreshed.

As described above, this time criticality 450 is used by the system to determine the priority order or event sequence 462, 464, 466, 468 at various points in time. In the example shown, at time T, the order 462 for the data planes A, B, C and E are as shown, namely plane A is assigned a portion of the available bandwidth first at point 472, followed by plane B at point 474, then plane C at point 476 and finally plane E is refreshed if the remaining bandwidth permits at point 478. This may be a preset root sequence as previously mentioned above. It can be appreciated that whether the remote data within and constituting a plane is refreshed depends on the comparison between the bandwidth requirement determined from the data plane analysis described above, and the available bandwidth.

After an additional amount of time, defined as Time T1 in FIG. 5, the ordering for the planes is unchanged, however in the scenario of time T1, there is insufficient bandwidth to refresh the data in planes C and E. If for example the available bandwidth between time T1 and time T2 is reduced or there is insufficient bandwidth still available to refresh all the planes, the system 400 alters the priority for the data planes, accordingly the event sequence 466 has changed.

As shown at point 466, plane C is now assigned the highest priority for refresh—in other words, plane C has the greatest or highest priority for using the available bandwidth at time T2. Plane A is demoted to third priority, with planes A and E unchanged. However, as shown, new data plane D 480 has been introduced, prompted by a change or introduction of new local data. Initially, new plane D is assigned a low priority, which indicates that it is not currently utilising or requiring remote data input.

The final order shown is order 468 at time T3. At this time, plane C is still the data plane prioritised to utilise the available bandwidth. Data refresh of the remote data in plane B is still ranked second most critical use of bandwidth, followed by plane A. Plane D has been promoted above plane E. A further new plane, plane F 482 is also shown as added to the overall process order.

From the examples shown in FIGS. 4 and 5, it is clear that the controller acts within the system to manage the received data in accordance with the available bandwidth, as well to alter a priority order for obtaining the remote data when the available bandwidth is insufficient to refresh all the remote data.

Figure 6:
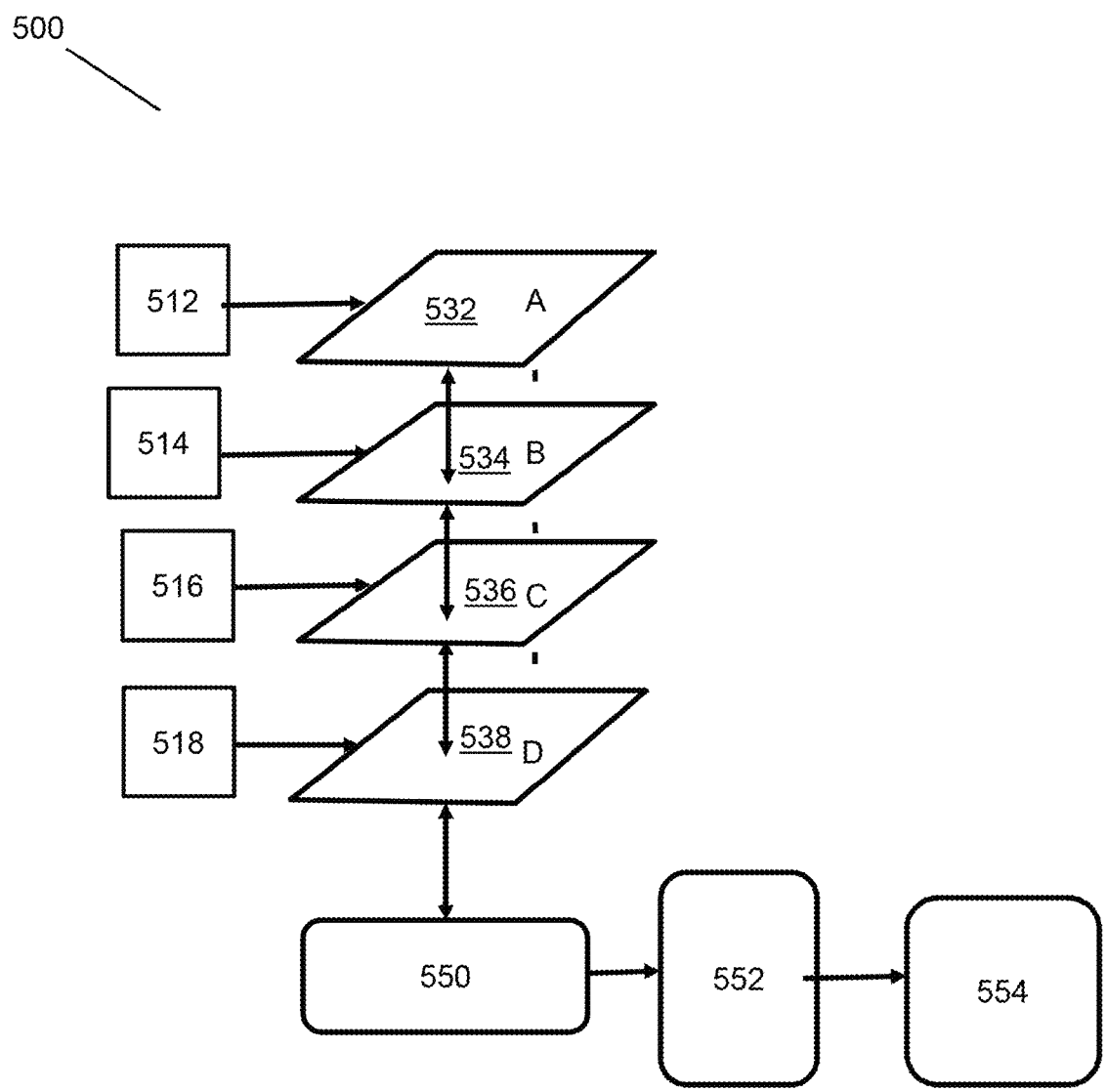
FIG. 6 is an alternative representation of the data plane structure of FIG. 3 according to an embodiment of the present disclosure.

FIG. 6 provides a further alternative and complimentary embodiment of a system flow or sequence 500. In this example, the local data 512, 514, 516, 518, (notionally representing the occupancy, media, vehicle dynamics and engine), form data planes 532, 534, 536 and 538.

The vehicle computer or controller 550 is configured to receive the local data 512-518, represented by the local data planes 532-538 in the form of status data 552. The status data 552 may be further decomposed to a more efficient form, such as a sparse matrix or tensor, depending upon the complexity of the status data. This compressed data 554 may then be used for data mining and optionally may be used for determining the future potential conditions, for example by utilising the computing power of an external server or computer. The data may also be used to analyse and ascribe risk to an event based on the local data.

Continuing the example of FIG. 6, consider a situation in which there are N of these simple risk indicators, each provided by the local data 512-518 obtained by sensors as described in relation to the earlier figures. The risks indicators can be aggregated over a time period to form a vector r of length N where the i'th component is given by the number of occurrences of each risk indicator over the time period. These vectors can then be further aggregated over a number of time periods by forming an N-rank risks tensor R where the components are given by the number of instances of the vector r with those components. For example, if two instances of the vector (0; 1; 3) were seen, then $R_{124}=2$; the offset of 1 in each component between (0; 1; 3) and (1; 2; 4) is so that the vectors which contain a zero component can be stored. As well as the risks vector, an N-rank scores tensor S is used which represents how each component contributes to the risk that a driver has exposed themselves to. In the real world, the values of this scores tensor would need to be determined by an insurance company, but for this example a very simple linear model can be used:

$$S_{ijk}=i+j+k+\ldots -N,$$

i.e. the score for each risk indication is simply the number of occurrences of that risk; the subtraction of N is just to undo the effect of adding one to each of the indices when creating the risk tensor so that a driver which exposed themselves to no risk factors is given a score of zero. Once the two tensors have been calculated, calculating the risk is simply a matter of calculating the product of the two tensors:

$$T = R_{ijk} \ldots S_{ijk} \ldots,$$

where the Einstein convention is used for the implicit sum over the suffixes.

Further data can be added easily to the tensor framework and the framework can be easily updated to provide a picture of how the risk to the driver evolves dynamically. The influence of outside remote data sources can also be considered, for example, the driving style and vehicle condition of other road users in proximity to the current road user/vehicle as has been extensively described above. This can be appreciated to be of particular use for a group of autonomous vehicles controlled without a driver.

Although the asset is described in relation to a vehicle, as detailed above, the asset may be a health device, such as a smart watch, smart fitness device or any other medical device that utilises local data sources together with remote data sources. By managing the order of priority in which the remote data sources are received, analysed or fetched, the available bandwidth can be managed. Health sensors may include health diagnostic sensors, such as heart rate and rhythm sensors, blood glucose level, etc.; activity sensors, such as movement sensors including accelerometers, gyrometers; body position sensors including gyrometers and altitude sensors; location sensors including GPS and wireless communication positioning sensors; and user status sensors, such as body temperature using a thermometer.

From reading the present disclosure, other variations and modifications will be apparent to the skilled person. Such variations and modifications may involve equivalent and other features which are already known in the art of receivers and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:

1. A controller for managing data demand to and from a vehicle, wherein the controller is configured to:
   obtain streams of local data from one or more vehicle sensors, said local data providing local information of a current condition of the vehicle;
   determine one or more potential future conditions of the asset vehicle based on the current condition of the vehicle and on changes in the local data;
   determine a bandwidth requirement to obtain streams of remote data from one or more remote data sources, each stream being potentially relevant to the one or more potential future conditions of the vehicle;
   compare the bandwidth requirement to an available bandwidth; and
   determine a priority order for obtaining the streams of remote data if the available bandwidth is below the bandwidth requirement and is further configured to:
   assign a critical time value to each potential future condition that defines the time by which the potential future condition requires refreshed remote data.

2. The controller of claim 1 further configured to determine the priority order by calculating the relevance of the remote data to the one or more potential future conditions of the vehicle based on changes in the local data.

3. The controller of claim 2 further configured to dynamically alter the priority order to prioritise obtaining the remote data in order of relevance within the available bandwidth based on the changes in the local data.

4. The controller of claim 2, wherein the controller determines the order of relevance based on an event sequence describing a task priority for handling of the remote data.

5. The controller of claim 4, wherein the event sequence is dynamically altered based on the available bandwidth.

6. The controller of claim 4, wherein the event sequence further describes a task priority for handling of the local data.

7. The controller of claim 4, wherein the event sequence defaults to a root sequence defining a default task priority for handling of remote data if the available bandwidth is at or above the bandwidth requirement.

8. The controller of claim 7, wherein the event sequence defaults to the root sequence if the available bandwidth is insufficient to obtain any remote data sources.

9. The controller of claim 4, wherein the event sequence comprises one or more data planes of remote data and local data, said data planes defining the one or more potential future conditions.

10. The controller of claim 9, wherein a data plane is populated by: the remote data from the one or more remote data sources; and the local information from the one or more vehicle sensors.

11. The controller of claim 9, wherein each data plane has a downstream bandwidth requirement for obtaining the remote data from the one or more remote data sources; and an upstream bandwidth requirement for reporting the local data or changes in the local data to a remote server.

12. The controller of claim 11, wherein the bandwidth requirement is the sum of the upstream and downstream bandwidth requirements for every data plane.

13. The controller of claim 9, wherein the data planes combine the local and remote data based on a location of the vehicle.

14. The controller of claim 9, wherein the data planes are arranged in a tensor.

15. The controller of claim 9, wherein the data planes are arranged according to the event sequence.

16. The controller of claim 1, wherein the controller calculates a remote bandwidth required to obtain the remote data within the critical time value for a or each potential future condition.

17. The controller of claim 16, wherein the bandwidth requirement comprises the sum of the remote bandwidth required for all potential future conditions.

18. A system for managing data demand to and from a vehicle, said system comprising:
a controller for managing data demand to and from a vehicle, wherein the controller is configured to:
obtain streams of local data from one or more vehicle sensors, said local data providing local information of a current condition of the vehicle;
determine one or more potential future conditions of the vehicle based on the current condition of the vehicle and on changes in the local data;
determine a bandwidth requirement to obtain streams of remote data from one or more remote data sources, each stream being potentially relevant to the one or more potential future conditions;
compare the bandwidth requirement to an available bandwidth;
determine a priority order for obtaining the streams of remote data if the available bandwidth is below the bandwidth requirement; and
assign a critical time value to each potential future condition that defines the time by which the potential future condition requires refreshed remote data; and
an output channel associated with the controller and configured to transceive the streams of remote data to and from the controller.

19. A method of managing data demand for a vehicle, said method comprising the steps of:
receiving streams of local data from one or more vehicle sensors, said local data monitoring a current condition of the vehicle;
identifying changes in the current condition of the vehicle from changes in the vehicle sensors;
determining one or more potential future conditions of the vehicle based on the changes;
determining a bandwidth requirement for obtaining streams of remote data from one or more remote data sources relevant to the one or more potential future conditions for the vehicle; and
comparing the bandwidth requirement to an available bandwidth; and
prioritising the order in which the streams of remote data are retrieved, wherein the prioritising is based on a time criticality for refreshing the remote data.

20. The method of claim 19, wherein the prioritising is based on the bandwidth requirement of each stream of remote data.

* * * * *